Figure 1:
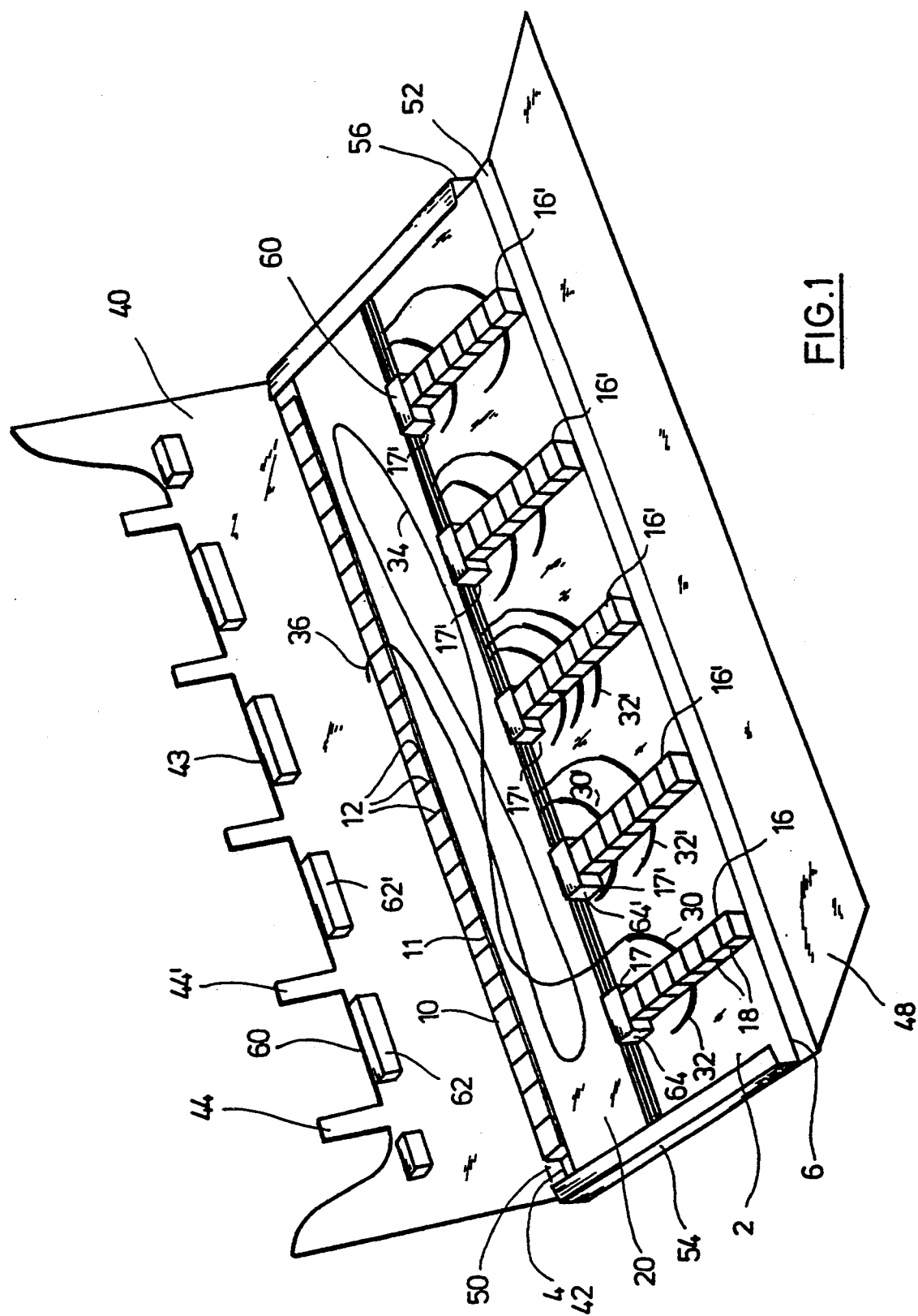

United States Patent [19]

Kettner et al.

[11] Patent Number: 5,344,005
[45] Date of Patent: Sep. 6, 1994

[54] PACKAGE WITH SUTURE MATERIAL FOR SURGICAL PURPOSES

[75] Inventors: Ralf Kettner, Lubeck; Dieter Brunken, Huettblek, both of Fed. Rep. of Germany

[73] Assignee: Ethicon, Inc., Somerville, N.J.

[21] Appl. No.: 78,698

[22] Filed: Jun. 17, 1993

[51] Int. Cl.⁵ ............................................. A61B 17/06
[52] U.S. Cl. .................................................. 206/63.3
[58] Field of Search ........................................ 206/63.3

[56] References Cited

U.S. PATENT DOCUMENTS

| | | | |
|---|---|---|---|
| 4,135,623 | 1/1979 | Thyen | 206/63.3 |
| 4,391,365 | 7/1983 | Batchelor | 206/63.3 |
| 5,249,672 | 10/1993 | Brown et al. | 206/63.3 |

*Primary Examiner*—William I. Price
*Attorney, Agent, or Firm*—Paul A. Coletti

[57] ABSTRACT

The invention relates to a package with suture material for surgical purposes, especially as an inner package for sterile packaging. A bottom plate (2) displays in its rear zone a rear carrier strip (10) and in the front zone several transverse carrier strips (16, 16') running perpendicular thereto. Needles (32, 32') of needle/thread combinations (30, 30') or the front ends of single threads are held by guide cuts (18) of the transverse carrier strips (16, 16'). The threads (34) are divided into groups, preferably the threads (34) of the needle/thread combinations (30) allocated to a specific transverse carrier strip (16) being separated from the threads of others by intermediate sections (20). The rear zone of the bottom plate (2) is covered by a cover plate (40) and the front zone by a closure plate (48) which is opened during use.

3 Claims, 4 Drawing Sheets

PACKAGE WITH SUTURE MATERIAL FOR SURGICAL PURPOSES

The invention relates to a package with suture material for surgical purposes, in particular as an inner package for sterile packaging.

Surgical suture material is used in the form of threads reinforced with needles, i.e. needle/thread combinations, and in the form of single threads in pre-cut lengths. Various types of material such as e.g. silk, polyamides, polypropylene or woven polyesters and resorbable materials are available in various thread thicknesses and thread lengths for the sutures. A number of different straight and bent needles, varying in needle size, needle thickness and type of ground section, are used to reinforce the threads.

Surgical suture material must be packaged so as to ensure that the contents are kept secure and sterile. The material is to be removable quickly and safely without entanglements of the single threads, and a further aim is that the threads, once removed, do not tend to regain something of the shape in which they lay in the package ("thread memory").

It has been usual thus far to supply surgical suture material in the form of one or more needle/thread combinations, similar in terms of material type, thread thickness, thread length and needle type, or single threads in a double-sterile package, i.e. enclosed in a primary package and a secondary package. Before or during the operation the OT staff passing over material, who are not working in a sterile ambience, have to open the secondary packaging (overwrap) of the pack in question so that the OT staff who are working in a sterile ambience can grasp the sterile primary package and, after opening the primary package, remove the needle/thread combinations or single threads contained therein and pass them on to the doctor performing the operation. This mode of packaging results in a great burden being placed on the OT personnel. During more elaborate operations, in which several different needle/thread combinations or single threads are needed, such passing on of single articles is exceedingly-time-consuming.

The object of the invention is to propose a package or a packaging system with suture material for surgical purposes which makes it possible to have all the needle/thread combinations and/or single threads desired individually by an operator for a specific operation and needed for the operation in question available in the package in a double- or even single-sterile pack so that, after removal of the optionally present secondary package and of the primary package, this package with the whole of the needle/thread combinations or single threads necessary for the operation in question is available to the OT staff working in a sterile ambience, the said staff then passing the needle/thread combinations or single threads on to the operator.

To achieve this object, a package with suture material for surgical purposes is proposed which is formed in accordance with the main claim, other advantageous versions being mentioned in the subsidiary claims.

The result of this is that all the suture material needed for an operation is available in a single package (or, in the case of major operations requiring much suture material, in a few packages). There is no time-consuming opening of numerous single packages. There is a saving of space for storage; moreover, unnecessary waste such as would occur when using numerous single packages is avoided. Because the needles or front thread ends are clearly arranged on the transverse carrier strips, errors during the removal of the suture material from the package are virtually ruled out. The intermediate sections and, where appropriate, the guide bar ensure that the threads do not hook under one another. This guarantees problem-free removal during use.

Figure 2:
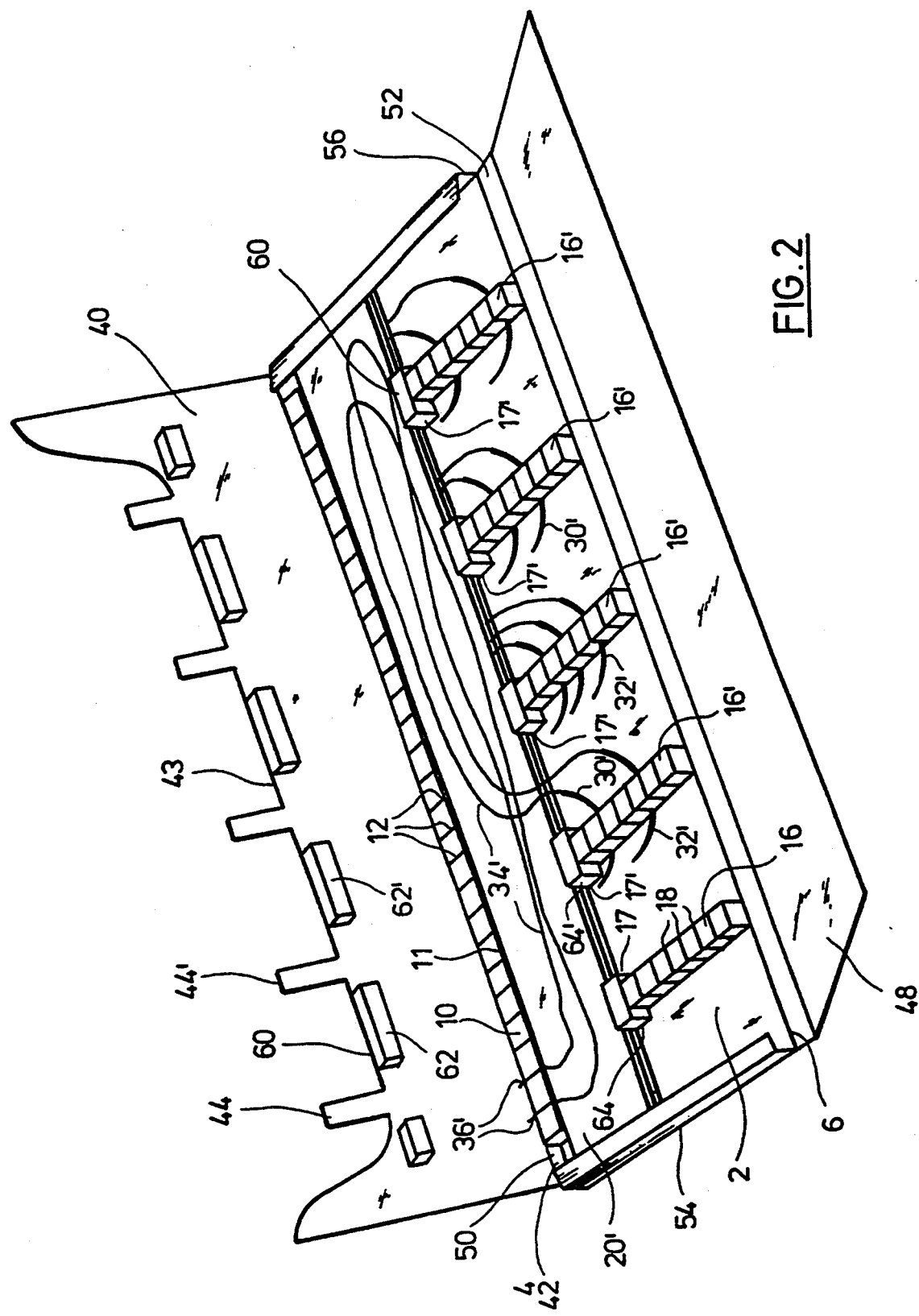
Figure 3:
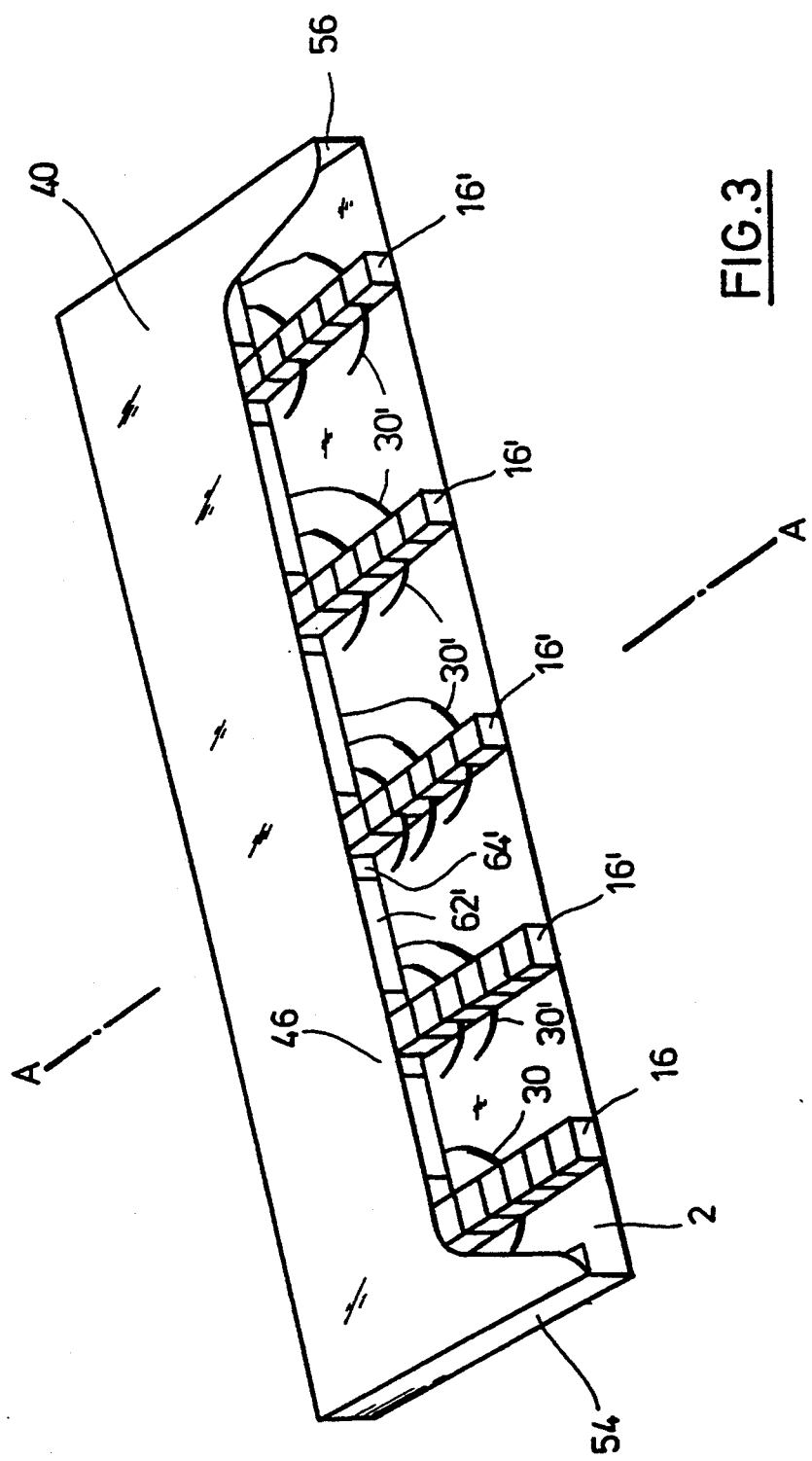
Figure 4:
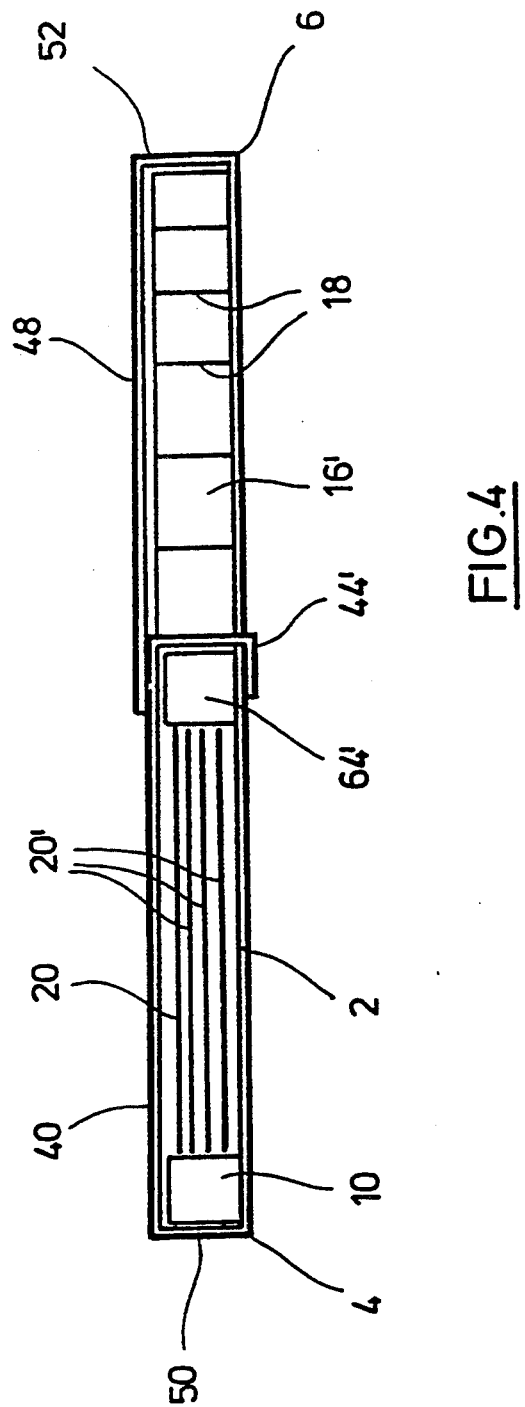

The invention is described below with reference to an embodiment. The drawings show:

FIG. 1: a perspective view of a package according to the invention with raised cover plate and opened-up closure plate;

FIG. 2: a perspective view of a package according to the invention in which, compared with the situation shown in FIG. 1, the needle/thread combination on the left is taken out and the topmost intermediate section is removed for clarification;

FIG. 3: a perspective view of a package according to the invention in the as-used state, the closure plate having been taken away; and FIG. 4: a cross-section through a package according to the invention along the line A—A from FIG. 3, the closure plate being in the shut position.

The package according to the invention has a bottom plate 2 which is preferably rectangular and has a longitudinal format with a rear longitudinal edge 4 and a front longitudinal edge 6, see FIG. 1 and FIG. 4. Parallel to the longitudinal edges 4, 6 in the rear zone of the bottom plate 2, a rear carrier strip 10 with guide cuts 12 open to the top is secured on bottom plate 2. The rear carrier strip 10 can also consist of several pieces arranged with gaps in between in the direction of the rear longitudinal edge 4. Arranged in the front zone of bottom plate 2 are several transverse carrier strips 16, 16' which run perpendicular to longitudinal edges 4, 6. They extend roughly from the front longitudinal edge 6 to their rear ends 17, 17' which lie roughly in the middle zone of the bottom plate 2. The transverse carrier strips 16, 16' are also provided with guide cuts 18 open to the top.

Preferably, a single specific type of a needle/thread combination 30, 30' (or a few types, different but clearly distinguishable from one another) is allocated to every transverse carrier strip 16, 16', the material type, thickness and length of the thread and the needle type being the same for a given type. These allocations allow the suture material to be clearly arranged in the package. The needles 32, 32' of the needle/thread combinations 30, 30' are placed in the guide cuts 18 of the transverse carrier strips 16, 16'. The associated threads 34, 34' run essentially in the rear zone of the bottom plate 2 and their thread-end zones 36, 36' are in guide cuts 12 of the rear carrier strip 10. Threads 34, 34' preferably run in loops, as shown in FIGS. 1 and 2, whereby points with too small a curvature radius, and thus a "thread memory", are avoided. Instead of needle/thread combinations 30, 30', single threads can also be allocated to a transverse carrier strip 16, 16', the front ends of said threads then being located in guide cuts 18 of transverse carrier strips 16, 16'; a partial fitting with single threads is also possible.

In order to prevent thread 34 from becoming tangled or knotted with other threads 34' upon removal of a needle/thread combination 30 or of a single thread, threads 34, 34' are divided into groups, the threads of a specific group being separated from those of the others by intermediate sections 20, 20'. The division into groups is preferably carried out in such a way that the threads 34 allocated to a specific transverse carrier strip 16, i.e. the threads 34 of the needle/thread combinations 30 whose needles 32 are held in this transverse carrier strip 16, are separated from the threads 34' of the needle/thread combinations 30' allocated to the other transverse carrier strips 16' by the intermediate sections 20, 20'. FIG. 2 shows a package according to the invention as per FIG. 1, except that the needle/thread combination 30 lying furthest to the left in FIG. 1 has been taken out and the intermediate section 20 lying uppermost in FIG. 1 removed for clarification; compare also FIG. 4. The intermediate sections 20, 20' consist of a thin material, for example parchment paper, and extend essentially in the zone between the front longitudinal edge 11 of rear carrier strip 10 and the rear ends 17, 17' of the transverse carrier strips 16, 16'.

The rear zone of the bottom plate 2 is covered by a cover plate 40, see also FIG. 3. The cover plate 40 is connected via its rear longitudinal edge 42, preferably in a material-uniform manner, to the rear longitudinal edge 4 of the bottom plate 2, preferably via a rear longitudinal side wall 50 designed as a double fold. If the cover plate 40 is laid round onto the bottom plate 2 in the ready-assembled package, see FIG. 2, the free longitudinal edge 43 of the cover plate 40 preferably runs roughly along the rear ends 17, 17' of the transverse carrier strips 16, 16'. In an advantageous version, restraining elements 44, 44' start from the free longitudinal edge 43 in the area of transverse carrier strips 16, 16' and are preferably connected in material-uniform manner to cover plate 40. The restraining elements 44, 44' are bent downwards from the cover plate 40 and inserted through slits in the transverse carrier strips 16, 16' and the bottom plate 2 and laid round at the back of the bottom plate 2, see FIG. 4. In this way, the free longitudinal edge 43 of the cover plate 40 is fixed vis-a-vis bottom plate 2 at the points where transverse carrier strips 16, 16' extend.

Marks and inscriptions 46 can be printed on the cover plate 40, the former showing which types of needle/thread combinations 30, 30' or single threads are allocated to a specific transverse carrier strip 16, 16'.

The front zone of the bottom plate 2, i.e. the zone in which the needles 32, 32' are located, is covered by an closure plate 48 when the package according to the invention is sealed. The closure plate 48 is connected to the bottom plate 2, preferably in a material-uniform manner, preferably via a longitudinal side wall 52 designed as a double fold. When the package is used it can be advantageous to separate the opened-up closure plate 48 completely from the bottom plate 2, see FIG. 3, for which reason a perforation can be provided along the front longitudinal edge 6 of the bottom plate 2. Preferably located at the narrow sides of the package are transverse side walls 54, 56 which can be designed to be integral with the bottom plate 2, the cover plate 40 and/or the closure plate 48 and which branch off from these parts.

The removal of a needle/thread combination 30 from the package can be facilitated by a guide bar 60 in an advantageous version of the invention. The guide bar 60 runs parallel to the longitudinal edges 4, 6 of the bottom plate 2 in the area of the rear ends 17, 17' of the transverse carrier strips 16, 16'. In the embodiment shown in FIGS. 1 and 2, the guide bar 60 is divided into several pieces 62, 62' and 64, 64'. The pieces 62, 62' running between the ends 17, 17' of the transverse carrier strips 16, 16' are secured along the free longitudinal edge 43 of the cover plate 40 at its underside. The pieces 62, 62' can also be dispensed with. The pieces 64, 64' lie directly behind the rear ends 17, 17' of the transverse carrier strips 16, 16' and are secured on the bottom plate 2. They are each somewhat longer than the width of the transverse carrier strips 16, 16', as a result of which the guide zone for a given thread 34, 34' is somewhat narrower than the distance between two transverse carrier strips 16, 16', which proves advantageous during use.

To facilitate the picking up of the needles 32, 32' from the guide cuts 18 of the transverse carrier strips 16, 16', prepared punched-out sections can be arranged in the bottom plate 2 (not shown in the Figures). For example, essentially rectangular fields can be provided to the right of the transverse carrier strips 16, 16' (compare FIG. 1), the left-hand longitudinal sides of said fields being adjacent to the right-hand longitudinal edges of the transverse carrier strips 16, 16' and somewhat shorter than the latter, and their right-hand longitudinal edges running roughly in the middle between and parallel to two transverse carrier strips 16, 16'; a corresponding field can be provided to the right of the transverse carrier strip 16' lying furthest to the right. The bottom plate 2 is preferably punched through at the two narrow sides and at the right-hand longitudinal side of the fields, but not at the left-hand longitudinal side. Thus, before the removal of the needle/thread coordinations 30, 30' (or single threads), the desired fields can be folded away downwards around their left-hand longitudinal side. Removal is facilitated by the openings formed in this way in the bottom plate 2.

The rear carrier strip 10, the transverse carrier strips 16, 16' and/or, where appropriate, the guide bar 60 are preferably made from plastics material, in particular from flexible or foamed plastics material. The bottom plate 2 with cover plate 40 and closure plate 48 preferably consists of cardboard.

The whole of the package with suture material for surgical purposes according to the invention is made available, sterilized and closed and in separate outer packaging, with the types of needle/thread combinations or single threads necessary for the surgical measures in question. The outer packaging can consist of an outer secondary package and an inner, sterile primary package, or of just a single package. After the outer packaging has been opened by OT personnel not working in a sterile ambience, under conditions in which the package according to the invention remains sterile, the OT personnel working in a sterile ambience need only to grasp the package according to the invention and open the closure plate 48 and, where appropriate, tear it off along the perforation at the front longitudinal edge 6 of the bottom plate 2. The cover plate 40 remains closed during this procedure, i.e. turned down onto the bottom plate 2, so that the rear zone of the bottom plate 2 with the threads 34, 34' is covered. The needle 32 of a needle/thread combination 30 or the end of a single thread can now be picked up without difficulty from a specific transverse carrier strip 16, whereupon the whole needle/thread combination 30 or the whole single thread can be out of the package and passed to the operator.

We claim:

1. Package with suture material for surgical purposes, in particular as an inner package for sterile packaging characterized by (a) a bottom plate with a rear carrier strip, the latter running in the rear zone parallel to the longitudinal edges of the bottom plate and being secured on said bottom plate, consisting of several partial sections and having guide cuts open to the top, and with several transverse carrier strips, the latter running in the front zone perpendicular to the longitudinal edges of the bottom plate being secured on said bottom plate and having guide cuts open to the top;

(b) at least one intermediate sections which extends essentially in the zone between the front longitudinal edge of the rear carrier strip and the rear ends of the transverse carrier strips;

(c) a plurality of needle/thread combinations, the needles of which are held in guide cuts of the transverse carrier strips and the thread-end zones of which are held in guide cuts of the rear carrier strip, the threads being divided into groups which are separated from one another by the intermediate sections;

(d) a cover plate which is connected to the rear longitudinal edge of the bottom plate and can be turned onto the bottom plate, covering in its areal extension said bottom plate roughly as far as the rear ends of the transverse carrier strips; and (e) a closure plate which is connected to the front longitudinal edge of the bottom plate and is so dimensioned in its areal extension that, after being turned down onto said bottom plate, it covers the front zone of the bottom plate not covered by the cover plate.

2. Package according to claim 1, characterized in that the division of the threads into groups is such that the threads of the needle/thread combinations allocated to a specific transverse carrier strip are separated from one another by the intermediate sections from the threads of those needle/thread combinations allocated to other transverse carrier strips.

3. Package according to claim 1 or 2, characterized in that the cover plate and the closure plate are connected to the bottom plate via longitudinal side walls designed as a double fold.

* * * * *